United States Patent [19]

Wessling et al.

[11] Patent Number: 5,508,035
[45] Date of Patent: Apr. 16, 1996

[54] STABLE CONCENTRATES AND EMULSIONS OF WATER-INSOLUBLE ORGANIC PESTICIDES

[75] Inventors: Ritchie A. Wessling, Berkeley, Calif.; Dale M. Pickelman, Auburn; Dennis G. Wujek, Midland, both of Mich.

[73] Assignee: DowElanco, Indianapolis, Ind.

[21] Appl. No.: 145,055

[22] Filed: Oct. 27, 1993

Related U.S. Application Data

[63] Continuation of Ser. No. 400,420, Aug. 30, 1989, abandoned, which is a continuation-in-part of Ser. No. 239,244, Sep. 1, 1988, abandoned.

[51] Int. Cl.$^6$ .......... A01N 25/04; A01N 25/08; A01N 25/24
[52] U.S. Cl. .......... 424/405; 424/407; 424/409; 514/772.4
[58] Field of Search .......... 514/272.4, 407, 514/405, 419; 523/122

[56] References Cited

U.S. PATENT DOCUMENTS

| | | | |
|---|---|---|---|
| 3,400,093 | 9/1968 | Feinberg | 260/29.6 |
| 4,036,788 | 7/1977 | Steckler | 514/295 |
| 4,199,363 | 4/1980 | Chen | 430/512 |
| 4,203,716 | 5/1980 | Chen | 430/207 |
| 4,303,642 | 12/1981 | Kangas | 424/78 |
| 4,337,185 | 6/1982 | Wessling et al. | 524/458 |
| 4,470,966 | 8/1984 | Costanza et al. | 424/81 |
| 4,544,697 | 10/1985 | Pickelman et al. | 524/458 |

FOREIGN PATENT DOCUMENTS

| | | |
|---|---|---|
| 0096103 | 6/1982 | European Pat. Off. . |
| 0289356 | 4/1988 | European Pat. Off. . |
| 2285431 | 9/1975 | France . |
| 3304457 | 2/1983 | Germany . |

OTHER PUBLICATIONS

Rogiers et al., "Novel Trends in Dispersants", Sixth International Congress of Pesticidal Chemistry, Ottawa, Canada, Aug. 10–15, 1986.

*Primary Examiner*—Edward J. Webman
*Attorney, Agent, or Firm*—S. Preston Jones; Donald R. Stuart

[57] ABSTRACT

Stable emulsions of water-insoluble organic pesticides are formed by mixing the pesticide with an aqueous dispersion of a graft copolymer comprising a reactive polymeric surfactant base polymer and a nonionic hydrophobic grafted composition. The graft copolymer spontaneously absorbs organic pesticides with low water solubility upon simple mixing. The resulting product is much more stable to coalescence than emulsions made with conventional or polymeric surfactants.

Emulsifiable organic based concentrates, having a continuous oil phase, which are formed from admixtures of pesticidally active water-insoluble organic pesticides with graft copolymers can be diluted with or in water, thus, inverting the continuous oil phase to stable water based oil-in-water emulsions of the active pesticide.

2 Claims, No Drawings

STABLE CONCENTRATES AND EMULSIONS OF WATER-INSOLUBLE ORGANIC PESTICIDES

CROSS-REFERENCE TO RELATED APPLICATION

This is a continuation of application of Ser. No. 07/400,420 filed Aug. 30, 1989, now abandoned, which is a continuation-in-part of Ser. No. 07/239,244 filed Sep. 1, 1988, now abandoned.

BACKGROUND OF THE INVENTION

As shown in U.S. Pat. No. 3,400,093 issued Sep. 3, 1968 to Irving Feinberg, known methods for incorporating water-insoluble organic pesticides into water-based systems have been unsatisfactory in that the pesticides tend to settle out and do not remain uniformly dispersed in said systems. Feinberg proposed to solve that problem by emulsion polymerization of vinyl-type monomers in the presence of the pesticide. However, certain pesticides, such as chlorpyrifos and chlorpyrifos-methyl, tend to hydrolyze if heated to polymerization temperatures for extended periods of time and, in addition, the presence of a pesticide in a monomer will influence the polymerization to some degree, e.g., the rate of polymerization, the conversion and/or the molecular weight of the polymer produced.

Kangas, in U.S. Pat. No. 4,303,642 issued Dec. 1, 1981, proposed to solve the above problems by adding the pesticide to a finished latex wherein the polymeric particles were in a size range of from 0.03 to 20 microns, and increases in pesticide efficiency were indeed demonstrated, although optimum stability and transfer of the pesticide through soil were not obtained.

Rogiers and Bognolo, in a paper presented at the Sixth International Congress of Pesticide Chemistry, Ottawa, Canada, Aug. 10–15, 1986, reported on the stabilization of an Ethirincol suspension concentrate with a graft stabilizer of a polymethylmethacrylate-polymethacrylic acid grafted with polyethylene oxide.

T. J. Chen, in U.S. Pat. Nos. 4,199,363 and 4,203,716, discloses a process for uniformly dispersing hydrophobic materials through hydrophilic colloid layers, such as photographically useful layers containing gelatin.

Soil pesticides are usually incorporated into the soil mechanically or are spread on the surface to be leached into the soil by rainfall. In either case, the pesticide may not be able to function properly because it becomes immobilized at the point of application. This will certainly be the case for large hydrophobic molecules and the problem is compounded further if the carrier is itself a large hydrophobic particle.

SUMMARY OF THE INVENTION

In accordance with this invention, stable aqueous emulsions of water-insoluble organic pesticides are formed by mixing the pesticide with an aqueous dispersion of a graft copolymer (carrier) comprising a ionic reactive polymeric surfactant (RPS) base polymer and a nonionic hydrophobic grafted composition. It has been found that the said graft copolymer spontaneously absorbs organic pesticides with low water solubility upon simple mixing. The resulting product is much more stable to coalescence than emulsions made with conventional surfactants. If not itself liquid, the organic pesticide can be dispersed in the aqueous dispersion by first melting or dissolving it in a water-insoluble organic solvent.

Because the graft chains are completely water insoluble they prevent the graft copolymer aggregates from dissolving into free molecules. The graft chains can be selected to have a high affinity for the material (pesticide) to be emulsified and once formed the emulsion is very stable because the stabilizing polymeric surfactant on the surface is chemically bound on the surface of a particle by the graft chains that are dissolved in it, which particle is an aggregate comprised of the RPS graft, pesticide and water insoluble additives in which the graft chains and water insoluble components are mutually compatible.

An anionic hydrophilic organic backbone provides stabilization against flocculation or adsorption on the soil particles. A cationic hydrophilic organic backbone also provides stabilization against flocculation and enhances wetting and adhesion to foliage.

In the compositions of this invention, the graft chains form the dispersed particle and the backbone forms the stabilizing surface. The graft copolymerization process allows each component to be independently optimized to provide the most effective desired emulsion.

DETAILED DESCRIPTION OF THE INVENTION

The reactive polymeric surfactant base polymers that can be used in the present invention include some of the cationic polymers described in U.S. Pat. No. 4,337,185 and the anionic polymers described in U.S. Pat. No. 4,427,819, which are incorporated herein by reference thereto. Such polymers advantageously have a hydrophilic backbone and a grafted hydrophobic side-chain. These polymers spontaneously aggregate to form non-dissociating polymeric micelles. These micellar structures are the seed particles mentioned in the above-referenced patents.

The aqueous based polymeric micelles are mixed directly with a liquid pesticide at ambient conditions or heated to liquify a crystalline pesticide until a homogeneous dispersion results. In order for the polymeric micelle to accommodate significant levels of the hydrophobic pesticide, the graft copolymer composed of an ionic main chain with pendant nonionic graft chains must stay at the surface of the particle to provide colloidal stability and therefore must not be crosslinked, i.e., must not be a microgel.

Water miscible coupling solvents can also be incorporated as an aid for the movement of the pesticide through the aqueous phase to the particle. The coupling solvent, e.g., acetone, methyl ethyl ketone, tetrahydrofuran, a $C_1$–$C_4$ alcohol, can be optionally, stripped from the mixture after the pesticide is incorporated.

It may be advantageous to employ other additives to aid in the preparation of the formulations. A cosurfactant, such as a ethylene oxide nonionic adduct of alkyl phenols having a hydrophilic-lipophilic balance value (HLB) in the range of from about 10 to about 13, can be used to facilitate transfer of pesticide or a plasticized pesticide solution through the aqueous phase to the hosting particle.

Water insoluble cosolvents or plasticizers of low volatility are also useful in preparing the formulations of the present invention. They are used to form plasticized particles which are solutions of the pesticides and cosolvents in the particles that remain non-crystalline for optimum low temperature stability and allow for reconstitution of formulations after freeze-thaw cycling. It is desirable for the cosolvent to be water insoluble and compatible with both the pesticide and the hydrophobic graft chains of the graft copolymer. This gives desirable water-based formulations with excellent stability, dilutability and movement in the soil.

Cosolvents of choice include plasticizing methyl esters of fatty acids such as caproic, lauric, myristic, oleic and tallowic; glycerides such as the oils of cottonseedy soybean, castor bean, and corn; triacetin, Citroflex® A4, and alkyl aromatics. Preferred plasticizers are Citroflex® A4 and the methyl esters of caproic, lauric, myristic, and oleic acid.

Preferred cosurfactants for optimum stability are polyoxylated nonylphenols where the average number of moles of ethylene oxide ranges from about 4 to about 10.

Polymers and pesticides can also be blended with a cosolvent and/or cosurfactant and then dispersed in water by a phase inversion process which provides an oil-in-water emulsion similar to that obtained via the aforementioned direct emulsion method. The anionic particles are, once formed in water, in a colloidal sense, very stable, maintaining their identity in the soil and functioning as a reservoir of pesticide, which when applied to the ground, can move very well through the soil. The cationic particles are also stable in a colloidal sense, and when sprayed aerially provide enhanced adhesion to foilage and, if desired, they provide immobilization of the pesticide on the soil surface for special pesticidal uses.

An emulsifiable concentrate can be formed by mixing the RPS/GRAFT Copolymer, nonionic cosurfactant, active pesticide, and a coupling solvent if needed to solvate the pesticide with the copolymer and then stripping off the solvent and water to form a non-aqueous based concentrate. A preferred process involves addition of pesticide or plasticized pesticide solution to a nonaqueous mixture of RPS/GRAFT Copolymer and nonionic cosurfactant to form an emulsifiable concentrate. Addition of a coupling solvent to this formulation is not an essential part of the concentrate, however, desirable coupling solvents are those possessing a low volatility, such as, for example, tetrahydrofural alcohol, various alkoxy alkanols, 1-methyl-2-pyrrolidinone, dimethylformamide and the like.

The use of an optional cosolvent and/or cosurfactant allows for the preparation of emulsifiable concentrates wherein a nonaqueous blend of RPS/GRAFT Copolymer, the active compound, cosolvent and/or cosurfactant can be subsequently dispersed in water to form an aqueous emulsion. The cosolvent must be compatible with the active ingredient (pesticide) and the hydrophobic polymeric sidechains of the RPS/GRAFT Copolymer. The cosolvent can be used to depress the melting point of the active ingredient, improve compatibility with the graft copolymer and aid in release of said ingredient when needed.

Generally the amount of the water insoluble organic pesticides which can be present in association with the ionic/nonionic graft copolymer is in the range of from about 1:50 to about 10:1 in terms of a weight ratio of the pesticide to the RPS/GRAFT Copolymer.

Desirable and preferred cosolvents and cosurfactants used for the preparation of stable emulsifiable concentrates are the same as those previously mentioned herein for the preparation of formulations by direct mixing of aqueous graft copolymer and pesticide.

Representative water-insoluble organic pesticides which can be employed in the practice of the present invention include one or more pesticides from the classes of acylurea insecticides, organophosphorous insecticides, pyrethroid insecticides, aryloxyaryl herbicides and sulfonamide herbicides. Examples of such pesticides include the acylurea insecticides described in U.S. Pat. Nos. 4,148,902; 4,173,637 and Re. 30,563, which are incorporated herein by reference, and especially 1-[3,5-dichloro-4-(( 5-trifluoromethyl)-3-chloro-2-pyridyloxy)phenyl]- 3-(2,6-difluorobenzoyl) urea (common name Chlorfluazuron);

the organophosphorous insecticides described in U.S. Pat. Nos. 3,244,586; 4,429,125; 4,654,329 and 4,729,987 which are incorporated herein by reference, especially chlorpyrifos and chlorpyrifos-methyl;

the pyrethroid insecticides such as cypermethrin, permethrin and fenvalerate;

the aryloxyaryl herbicides described in U.S. Pat. Nos. 4,550,192; 4,551,170 and 4,750,931 which are incorporated herein by reference, especially 2-(4-(((5-trifluoromethyl)-2-pyridinyl)oxy)phenoxy)propanoic acid; 2-(4-((3-chloro-5-trifluoromethyl)- 2-pyridinyl)oxy)-phenoxy)propanoic acid, methyl ester, 2-(4-((3-chloro-5-trifluoromethyl)- 2-pyridinyl)-oxy)phenoxy)propanoic acid,ethyl ester; and 2-(4-((3-fluoro-5-trifluoromethyl)- 2-pyridinyl)oxy)phenoxy)propanoic acid, methyl ester; and the sulfonamide herbicides described in U.S. Pat. Nos. 4,731,446; 4,740,233; 4,741,764 and 4,755,212 which are incorporated herein by reference, especially N-(2,6-dichlorophenyl)- 5,7-dimethoxy-1,2,4-triazolo(1,5 a)pyrimidine-2-sulfonamide; N-(2,6-dichloro- 3-methylphenyl)-5,7-dimethoxy-1,2,4-triazolo(1,5 a)-pyrimidine-2-sulfonamide; N-(2,6-dichlorophenyl)- 5-methyl-7-methylthio-1,2,4-triazolo-( 1,5a)pyrimidine-2-sulfonamide; N-( 2-trifluoromethylphenyl)-5-methyl-7-methylthio- 1,2,4-triazolo-(1,5a)-pyrimidine-2-sulfonamide; N-(2,6-dichloro-3-methylphenyl)-7-methoxy- 5-methyl-1,2,4-triazolo(1,5 a)-pyrimidine-2-sulfonamide; and N-(2,6-dichloro-3-methylphenyl)-7-ethoxy-5-methyl- 1,2,4-triazolo(1,5a)pyrimidine-2-sulfonamide.

The carrier employed to transport the pesticide should be a small hydrophilic colloidal particle with a high negative charge to promote rapid movement in the soil. In order to be effective, however, the particle must be stable against flocculation by polyvalent cations in the soil, and the ionic groups must be bound to the particle to avoid redistribution of the stabilizing groups, i.e., surfactant, to the surface of the soil particles. Because carboxylated latexes are not stable against flocculation by polyvalent cations they are not suitable for this use.

In conventional formulations the surfactants are absorbed on the particle surface and are in equilibrium with the aqueous phase and the surface of soil particles. Since the surface area is so larger the soil tends to act as an infinite sink of low surfactant concentration and much of the surfactant initially on the pesticide particle transfers to the soil, whereupon the pesticide particle either deposits on the soil or flocculates, thereby losing the ability to migrate through the soil. In the present invention the problem of a lack of the ability of the particle to migrate through the soil is avoided.

The preferred formulations are anionic and the reactive polymeric surfactant (RPS) in these cases is selected to optimize stability and migratory ability of the particle in the soil. Such surfactants are obtained by using a combination of pH independent anionic monomers and nonionic monomers. Combinations of sulfonate monomers and nonionic hydrophobic and hydrophilic units form the ionic backbone. Preferably, the backbone of the (RPS) is formed by the copolymerization of ethylenically unsaturated monomers.

The nonionic, hydrophobic units suitably are derived from any copolymerizable ethylenically unsaturated monomer which, when in the form of an amorphous homopolymer, would have a solubility in water of less than 0.1 percent. Specifically, styrene and/or methyl methacrylate function as the nonionic hydrophobic units. However, it should be noted that a backbone containing nonpolar sequences like styrene will require proportionately more ionic or hydrophilic units to achieve the same level of activity.

In some cases, it is advantageous to employ small amounts (e.g., usually less than about 15 weight percent and preferably from 0 to about 5 weight percent based upon the weight of the instant reactive polymeric surfactants) of very hydrophilic but not ionic comonomers for control of the surface activity and water solubility of the interpolymeric polyelectrolyte without having to use more of the ionic comonomers. Acrylamide, methacrylamide, hydroxyethyl acrylate and hydroxypropyl acrylate are particularly useful for this purpose.

Low concentrations of monomers with weak acid or weak base groups and salts thereof may also be used provided that the pH independence of the RPS is not substantially altered, e.g., a minor amount of a vinyl monomer such as acrylic acid or aminoethyl methacrylate (or the hydrochloride salt thereof) could be included to promote adhesion, serve as reactive sites and the like.

The RPS also contains grafting sites as described in the prior art. Grafting sites are typically vinyl groups linked to the backbone through an ester, amide or quaternary ammonium connection.

The side-chain composition copolymerized with these grafting sites is selected to compatibilize the cosurfactant and cosolvent with the active ingredient. The side-chain composition must be substantially hydrophobic and present in sufficient amount to render the graft copolymer aggregate nondissociable in water.

Preferably the graft polymer composition has a glass transition temperature (Tg) below the use temperature, preferably less than 30° C. (The Tg is easily determined using conventional differential thermal analysis.) Compatibility with the active ingredient can be tailored by copolymerizing the appropriate nonionic hydrophobic monomers. Selection can be made on the basis of a typical formulation scheme employing, e.g., known solubility parameters.

Typical monomers useful in preparing the side-chain graft polymers used in the invention include, for example, styrenics, acrylates, methacrylates, isoprene, butadiene, acrylonitrile, vinyl acetate, vinyl chloride, and vinylidene chloride. By copolymerization, the side-chain graft polymers having desired properties are obtained. Copolymer selections are made from known techniques for matching compatibility, solubility, and maintaining proper Tg.

The number and length of the graft chains can be optimized for specific formulations. Typically, the side-chain length should be minimized to facilitate rapid phase inversion of the emulsifiable concentrate. However, the molecular weight must be high enough to compatibilize with the oil phase and provide stability when diluted in water. Desirably the RPS/GRAFT Copolymers are sufficiently hydrolytically stable and resistant to biological attack to provide adequate life time of the particles in the soil.

The invention is further illustrated by the following examples wherein all parts are by weight unless otherwise specified.

EXAMPLE 1

Reactive Polymeric Surfactant (RPS) Having Pendant Methacrylate Groups

A base polymeric surfactant is prepared by adding 1000 parts of isopropanol and 650 parts of deionized water to a stirred reactor provided with a nitrogen atmosphere and maintained at 50° C. while continuously adding reactants from five separate sources with proportionate feeds over 120 minutes and the resulting polymerization is allowed to continue for an additional 2 hours. Feed compositions are as follows:

| Feed | Parts | Component |
|------|---------|---------------------------|
| 1 | 1000.00 | Deionized Water |
|   | 384.00  | 2-Sulfoethyl Methacrylate |
|   | 62.20   | Dimethylaminoethyl methacrylate |
| 2 | 554.00  | Methylmethacrylate |
| 3 | 6.18    | 2-Mercaptoethanol |
|   | 114.00  | Deionized Water |
| 4 | 2.00    | Tertiary(t)-butyl Hydroperoxide |
|   | 118.00  | Deionized Water |
| 5 | 1.50    | Sodium Formaldehyde Hydrosulfite |
|   | 118.50  | Deionized Water |

Twenty five hundred parts of deionized water are added followed by volatilization of 1700 parts. The resulting water soluble polymeric surfactant is converted to a reactive polymeric surfactant with pendant methacrylate vinyl sites by mixing with 56.3 parts of glycidyl methacrylate while heating for 2 hours at 50° C. (RPS$^\ominus$). The reactive polymeric surfactant, RPS$^\ominus$, has a solid content of 22.1 percent (21.8 percent solids by material balance), a total anionic charge of 1.87 milliequivalents per gram of solids and a number average molecular weight of less than 40,000.

EXAMPLE 2

Preparation of (RPS$^\ominus$/GRAFT) Copolymers

Hydrophobic styrene/2-ethyl hexyl acrylate copolymer chains are attached to water soluble reactive polymeric surfactant chains through emulsion copolymerization. A mixture is prepared by stirring 100 parts of each of styrene (S) and 2-ethyl hexyl acrylate (2-EHA) in an aqueous solution of 1448 parts of deionized water, 10 parts of isopropanol and 909 parts of RPS$^\ominus$ (22 percent solids by material balance). This monomer emulsion is heated to and maintained at 50° C. under a nitrogen atmosphere while adding proportionately from separate feed systems of 0.40 part t-butyl hydroperoxide in 50 parts of water and 0.30 parts sodium formaldehyde hydrosulfite in 50 parts water over about 30 minutes and heating continued for another 3 hours. An aliquot reveals (a) a 15 percent solids content indicating the reaction to be complete (b) a 0.94 milliequivalent anionic charge per gram solids and (c) a very small particle size as indicated by its translucent, bluish appearance. The designation for this RPS$^\ominus$ graft copolymer is:

$$\left( \frac{50/25/25}{RPS^\ominus/S/2\text{-}EHA} \right).$$

A portion was concentrated to 40 percent solids and still has a pourable viscosity at room temperature.

normal(n)-Butyl acrylate (n-BA) is substituted for 2-ethyl hexyl acrylate to make hydrophobic grafts on RPS$^\ominus$. A similar composition is:

$$\left(\begin{array}{c} 50/25/25 \\ RPS^\ominus/S/n\text{-BA} \end{array}\right).$$

EXAMPLE 3

Evaluation of RPS, RPS$^\ominus$/GRAFT Copolymers, Cosurfactant, and Cosolvent in Chlorpyrifos Formulations

| Components | Formulation | |
|---|---|---|
| | Non-Aqueous in parts by weight | Total in parts by weight |
| Chlorpyrifos | 2 | 2 |
| Cosolvent | 1 | 1 |
| Cosurfactant | 1 | 1 |
| RPS$^\ominus$/GRAFT Copolymer | 1 | Variable |
| Water | | Variable |
| | 5 | 10 |

The following formulation results show parameters for obtaining freeze-thaw stability:

(1) Cosurfactant

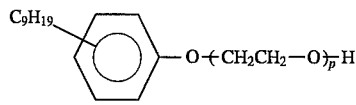

wherein p is an integer of from 5–9;
(2) Methyl laurate as cosolvent, and $$(3) \left(\begin{array}{c} 50/25/25 \\ RPS^\ominus/S/2\text{-EHA} \end{array}\right)$$

as (RPS$^\ominus$/GRAFT).

| COSURFACTANT | | | Formulation Stability | |
|---|---|---|---|---|
| P | Water Solubility | HLB[1] | Room Temp. | Freeze-Thaw |
| 4 | Insoluble | 8.8 | Slight Settling | Phase separation |
| 5 | Dispersible | 10.0 | Excellent | >3 cycles |
| 6 | Dispersible | 10.8 | Excellent | >3 cycles |
| 8 to 9 | Soluble | 12.2 | Very Slight Settling | >3 cycles |
| 9 | Soluble | 13.0 | Very Slight Settling | >3 cycles |
| 9 to 10 | Soluble | 13.3 | Very Slight Settling | Very Slight Settling |
| 15 | Soluble | 15.0 | 2-phases | Can't be tested |

[1]Hydrophilic-Lipophilic Balance (HLB) number.

Best cosurfactants for optimum freeze-thaw stability are the polyoxyethylated nonylphenols wherein (p) ranges from 5 to 9 and preferably 5 to 7 and the HLB values are from 10–13. It is noted that the cosurfactants wherein (p) is 4 or 15 and the HLB value is below 10 and above 13 are unacceptable. Acetyl tributyl citrate substitutes for methyl laurate and $$\left(\begin{array}{c} 50/25/25 \\ RPS^\ominus/S/n\text{-BA} \end{array}\right)$$

substitutes for the $$\left(\begin{array}{c} 50/25/25 \\ RPS^\ominus/S/2\text{-EHA} \end{array}\right)$$

in the preferable cosurfactant range.

EXAMPLE 4

Organic Based Concentrate Invertible to Stable Aqueous Emulsion by Reactive Polymeric Surfactant Graft Copolymers The following procedure is used to make an organic-based concentrate. A compatible mixture is formed with 300 parts of chlorpyrifos, 300 parts of polyoxyethylated nonylphenol (wherein p equals 8), 100 parts of Reactive Polymeric Surfactant Graft Copolymer (as solids in an aqueous dispersion)

$$\left(\begin{array}{c} 50/25/25 \\ RPS^\ominus/S/n\text{-BA} \end{array}\right),$$

and 1200 parts of isopropanol. The mixture is heated to about 50° C. and vacuum stripped to remove the isopropanol and most of the water. The loading is about 42 weight percent chlorpyrifos or 4 lbs./gallon. Small, stable oil-in-water particles are generated upon dilution in excess water. If the (RPS$^\ominus$/GRAFT) Copolymer is replaced with additional monomeric cosurfactant, the dilute oil-in-water particles phase separate in a short period of time, thus requiring agitation of the formulation to ensure uniform application.

EXAMPLE 5

Soil Penetration Evaluation

A formulation comprising in parts by weight

| | |
|---|---|
| Chlorpyrifos | 2.0 |
| Methyl Laurate | 2.0 |
| Cosurfactant (1) of Example 3 | 1.0 |
| RPS$^\ominus$/S/2-EHA | 1.0 |
| Deionized Water | 5.4 | was prepared. An amount containing 500 mg of formulated chlorpyrifos in 3.0 mL volume was diluted to 50 mL total volume with deionized water and introduced onto a 2 inch diameter 18 inch high column containing about 1150 grams dry soil (source is Midland, Mich.). The column was then eluted with about 650 mL deionized water and 450 mL of eluent was collected. The column was then frozen and cut into 4 equal quarters and analyzed for chlorpyrifos concentration by extracting the soil with cyclohexane. Two separate columns were tested with the following results:

| | Quarter | Mg Chlorpyrifos | Percent Distribution | Percent Recovery |
|---|---|---|---|---|
| Column A | 1 | 263.8 | 52.8 | |
| | 2 | 178.1 | 35.6 | 99.9 |
| | 3 | 51.1 | 10.2 | |
| | 4 | 6.7 | 1.4 | |

-continued

|  | Quarter | Mg Chlorpyrifos | Percent Distribution | Percent Recovery |
|---|---|---|---|---|
| Column B | 1 | 250.8 | 56.6 | |
| | 2 | 140.5 | 31.7 | 88.8 |
| | 3 | 41.6 | 9.4 | |
| | 4 | 10.6 | 2.4 | |

EXAMPLE 6

Pesticide Activity

The organic pesticides employed in the stable aqueous emulsion formulations of the water insoluble organic pesticide/polymeric micelle mixtures of the present invention have all been found to maintain their basic biological activity in the formulations of the instant invention as compared to the basic biological activity of the pesticides when the pesticide is used in conventional formulations. Formulations in accordance with the invention wherein the pesticide is chlorpyrifos are useful against, for example, corn rootworm and beet armyworm. Foliar and soil applications data are shown in Tables I and II respectively.

TABLE 1

Four-day residual toxicity of chlorpyrifos in formulation to beet armyworm on cotton leaves. Percent mortality was evaluated 72 hours after infestation

| Chlorpyrifos concentration (ppm) | Percent Mortality |
|---|---|
| 400 | 100 |
| 100 | 100 |
| 25 | 100 |
| 6.3 | 30 |
| 1.6 | 10 |
| control | 0 |

TABLE 11

Thirty-day residual toxicity of chlorpyrifos in formulation to western spotted cucumber beetle in California sandy loam soil. Percent mortality was evaluated 72 hours after

| Chlorpyrifos concentration (ppm) | Percent Mortality |
|---|---|
| 5.00 | 100 |
| 2.50 | 100 |
| 1.25 | 100 |
| 0.63 | 100 |
| 0.31 | 17 |
| 0.15 | 21 |
| control | 7 |

We claim:

1. A pesticidal formulation concentrate that can be diluted with water to form a stable oil in water emulsion, said concentrate comprising (1) a water insoluble organic pesticide; (2) an RPS/GRAFT copolymer comprised of a pH independent reactive polymeric surfactant and at least one nonionic hydrophobic monomer; and (3) a cosolvent; wherein the continuous phase is non-aqueous;

said copolymer comprises a hydrophilic ionic main chain with pendant hydrophobic nonionic graft chains;

said copolymer spontaneously aggregates to form non-dissociating polymeric micelles;

the grafted hydrophobic side chains are present in an amount sufficient so that the graft copolymer is insoluble in water and sufficient to provide compatibility with the oil phase and provide stability to the emulsion;

the number and length of the grafted hydrophobic side chains are sufficiently small so that reversible phase inversion occurs upon addition of water to the concentrate.

2. A concentrate as defined in claim 1 wherein the cosolvent is methyl laurate.

* * * * *